United States Patent [19]

Metzger

[11] Patent Number: 5,084,059
[45] Date of Patent: Jan. 28, 1992

[54] CORNEA TREPHINE INSTRUMENT

[75] Inventor: Daniel J. Metzger, Belleville, Ill.

[73] Assignee: Storz Instrument Company, St. Louis, Mo.

[21] Appl. No.: 503,887

[22] Filed: Apr. 4, 1990

[51] Int. Cl.⁵ ............................................ A61B 17/32
[52] U.S. Cl. ........................................ 606/166; 30/316
[58] Field of Search ............... 606/107, 161, 166, 184, 606/185, 167, 179, 187; 30/316

[56] References Cited

U.S. PATENT DOCUMENTS

| | | | |
|---|---|---|---|
| 2,473,968 | 6/1949 | Paton | 606/166 |
| 2,545,237 | 3/1951 | Maby | 30/316 |
| 2,838,050 | 6/1958 | Ara | 606/166 |
| 4,142,517 | 3/1979 | Stavropoulos | 606/179 |
| 4,190,050 | 2/1980 | Bailey | 606/166 |
| 4,205,682 | 6/1980 | Crock et al. | 606/166 |
| 4,319,575 | 3/1982 | Bonte | 606/166 |
| 4,336,805 | 6/1982 | Smirmaul | 606/166 |
| 4,352,242 | 10/1982 | Plet | 30/316 |
| 4,750,491 | 6/1988 | Kaufman et al. | 606/166 |
| 4,763,651 | 8/1988 | Kaufman et al. | 606/166 |
| 4,807,623 | 2/1989 | Lieberman et al. | 606/166 |
| 4,815,463 | 3/1989 | Hanna | 606/166 |
| 5,011,498 | 4/1991 | Krumeich et al. | 606/166 |

FOREIGN PATENT DOCUMENTS

| | | | |
|---|---|---|---|
| 0238196 | 8/1986 | Denmark | 606/166 |
| 0178034 | 1/1966 | U.S.S.R. | 606/166 |

Primary Examiner—C. Fred Rosenbaum
Assistant Examiner—William W. Lewis
Attorney, Agent, or Firm—Brooks & Kushman

[57] ABSTRACT

An ophthalmic device for making a circular incision in and alter the shape of the cornea of an eye has an inner body rotatably movable axially relative to an outer body to predetermine the depth of incision. A cornea stop is slidably moveable with the inner body to engage the cornea and position the device on the eye. The device is centered on the eye by means of a centering pin which is axially slidably moveable with respect to the cornea stop. A pointer located on the inner body operates in conjunction with a bezel on the outer body to provide a read-out of depth of the incision.

17 Claims, 2 Drawing Sheets

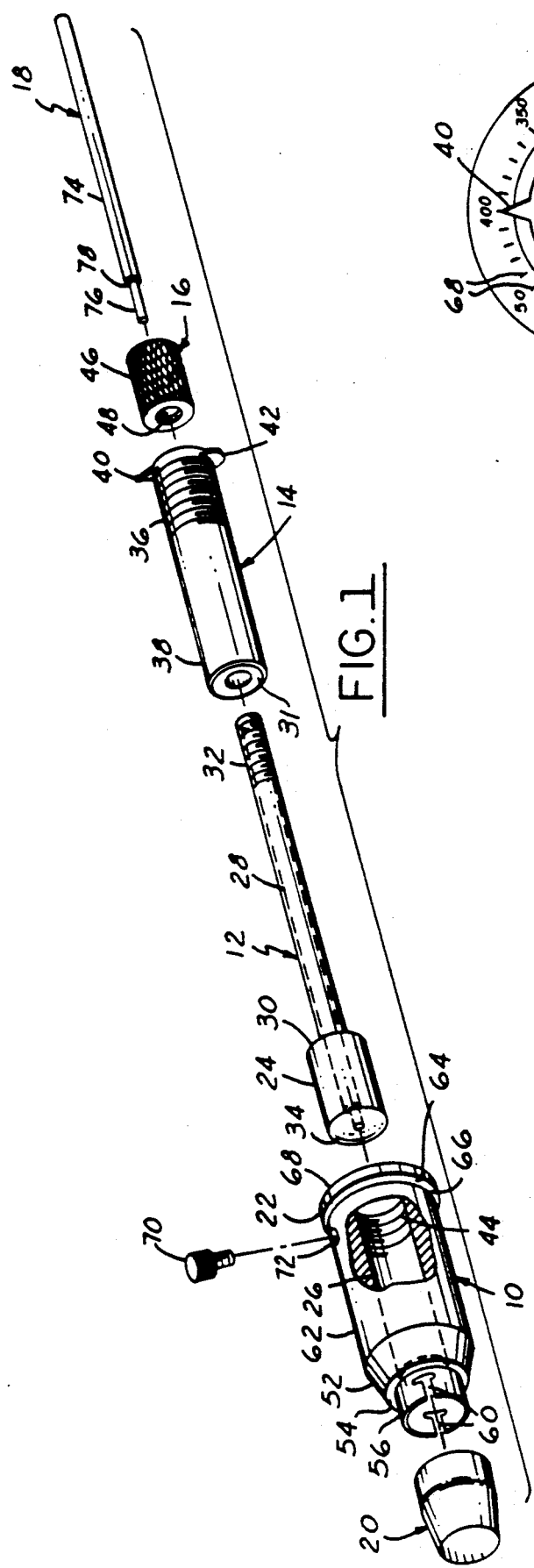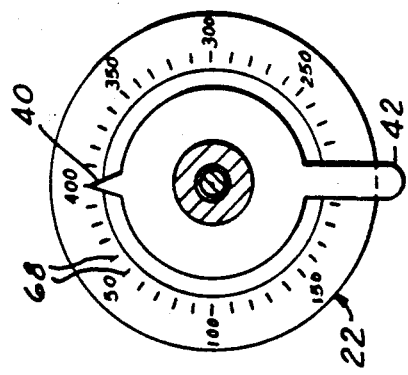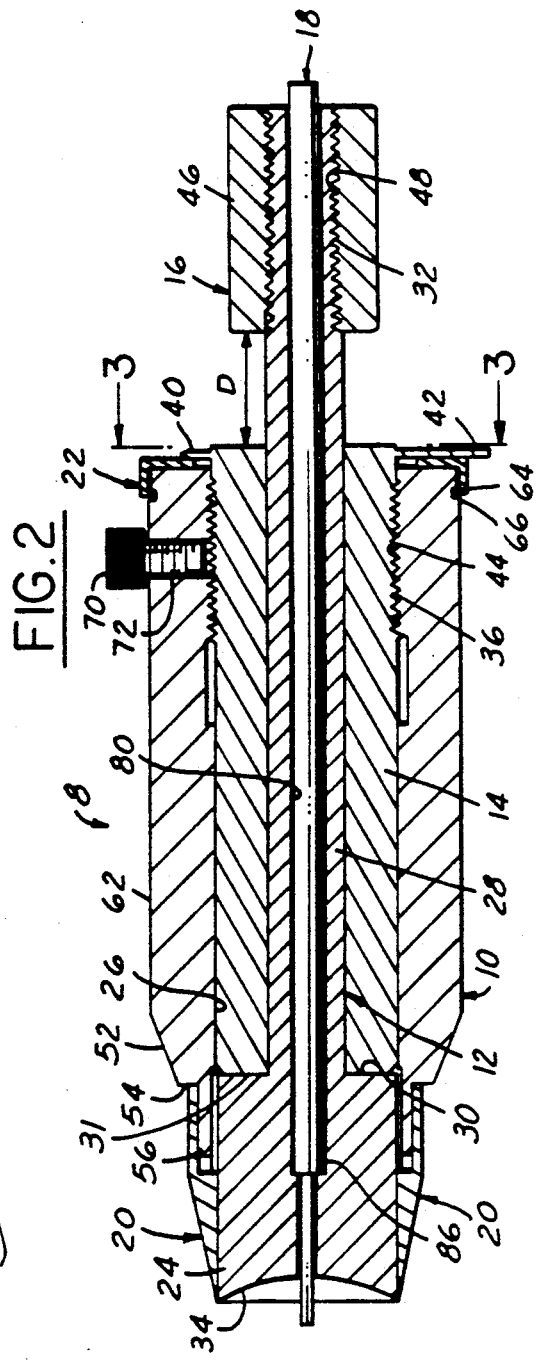

CORNEA TREPHINE INSTRUMENT

TECHNICAL FIELD

The present invention is related to the field of refractive corneal surgery, which involves surgical procedures to alter the shape of the cornea and thereby alter the refractive pattern of light passing through the cornea. In particular, the present invention is directed to a surgical instrument for forming incisions in the cornea which is useful, for example, in treatment of myopia (nearsightedness) or hyperopia (farsightedness).

BACKGROUND OF THE INVENTION

Myopia results from psychological imperfections in the eye of the patient which cause the focusing of the images in front of the retina. Surgical operations to correct myopia have typically involved techniques for effectively flattening the corneal surface in order to cause a posterior displacement of the focal point.

Hyperopia results from the physiological imperfections causing the focusing of images behind the retina, and a surgical technique used to correct this condition necessarily seeks to alter the patient's eye so as to achieve an interior displacement of the focal point.

Refractive corneal surgery for the correction of myopia is commonly referred to as a radial keratotomy. In this procedure a series of radial incisions are made in the cornea extending from the edge of the pupil outwardly to the limbus. These incisions serve to weaken the cornea causing intraocular pressure to displace the cornea so that the surface of the cornea flattens. Unfortunately, clinical results with this procedure have been characterized by significant variability of results.

An alternative refractive corneal surgical procedure for the correction of myopia has been developed where an annular wedge-like cut is made into but not completely through the cornea around a 360° path between the pupil and limbus. The cut walls are sutured together, causing a carefully controlled flattening of the corneal surface without structurally weakening the cornea or exposing the internal content of the eye to infection.

U.S. Pat. No. 4,807,623 to Lieberman discloses a trephine which is complex and provides for numerous adjustments of the blade. The device relies on a suction ring connected to the base to secure the device during surgery.

U.S. Pat. Nos. 4,750,491 and 4,763,651 to Kaufman et al. disclose a trephine of simple construction comprising a fixation member and two shafts each of which have a blade mounted thereon. The device relies on pressure applied by the user to control the depth of the incision and includes structure obscuring the incision. The fixation member relies on teeth to engage the sclera of the eye to secure the fixation member during surgery.

U.S. Pat. No. 4,336,805 to Smirmaul discloses a trephine containing a flexible drive shaft, ring gear and a drive pinion gear, increasing the size of the trephine and the difficulty of use, in addition to the requirement of operating a trephine with one hand while operating the device via the flexible drive shaft.

U.S. Pat. No. 4,190,050 to Bailey discloses a trephine which is power driven and relies on a vacuum source to secure it to the cornea. A blade is detachably connected to the handle so that it may serve as a storage container for a cornea. The requirement of the power source to operate the trephine decreases its portability, efficiency and increases the difficulty of use during surgery.

DISCLOSURE OF INVENTION

It is an object of the invention to provide an ophthalmic cutting device which obviates the problems associated with the use of the devices disclosed above.

The invention provides a trephine of simple construction which alows cutting of the cornea to a precise predetermined depth. An external body is provided with a locking screw which secures it to a rotatable and axially moveable internal body once a predetermined cutting depth has been selected. A cornea stop connected to a handle is abutted against the internal body and is positioned by the location of the internal body. A predetermined depth is selected by movement of the internal body relative the external body which is registered by a pointer attached to an arm which operates in conjunction with a movable bezel. The bezel contains increments located on its surface for the purpose of calibrating and predetermining the precise depth of the incision to be made during surgery.

Once calibrated, and the predetermined depth set, the locking screw locks the inner body and outer body together. A centering pin is axially slid through the entire unit to engage a predetermined spot marked on the cornea to center the device. The incision in the cornea is made by a cylindrical blade which is force-fitted against an expandable end of the outer body. While holding the handle and cornea stop stationary, the disposable blade, inner body, and outer body are rotated as a unit and the incision made to the predetermined depth.

The simple construction and slender shape of the device result in improved surgical techniques. The disposable blade associated with this device ensures improved safety through use of a constant and uniform edge of the blade as well as through the use of a new sterile blade for each surgery.

The ability to make a precise incision to a predetermined depth improves the surgical technique and enhances the safety of the surgical procedure.

Accordingly, it is a general object of my invention to provide an improved manually operable ophthalmic device which is easy to adjust for depth of incision and unobtrusive at the site of incision for ease of use.

It is also an object of the invention to provide an ophthalmic cutting device with a locking means for locking the outer body with respect to the inner body to position the blade with respect to the cornea stop and thereby facilitate making an incision to a predetermined precise depth.

It is a further object of the invention to provide an ophthalmic cutting device with a centering pin which is axially slidably with respect to the cornea stop and adapted to move in one direction to engage a cornea to locate the center of the eye so as to centrally position the outer body with respect to the cornea.

An additional object of the invention is to provide an ophthalmic cutting device with a pointer rotatable with the inner body and a bezel rotatably frictionally connected to one end of the outer body adjacent the pointer and calibrated to gauge the predetermined distance whereby to enable incisions of a predetermined depth.

An object of the invention is to provide an ophthalmic cutting device with a lever arm attached to the inner body opposite to the pointer and usable to adjust the rotation of the inner body relative to the outer body to set the predetermined distance.

It is a further object of the invention to provide an ophthalmic device for making incisions of predetermined depth in the cornea of the eye, the device having an outer body, an inner body rotatable relative to the outer body and a cornea stop. The device includes means cooperable between the inner and outer bodies to cause the outer body and inner body to move axially relative to each other for a predetermined distance when the inner body is manually rotated relative to the outer body to locate the cornea stop. The cornea stop is manually axially moveable with respect to the inner body and has at one end a curved cornea engaging surface and at its other end a manually gripped handle for moving the cornea stop in one direction against the inner body and in another direction for engaging a cornea.

The invention, together with additional features and advantages thereof, may best be understood by reference to the following description taken in connection with the accompanying illustrative drawings.

BRIEF DESCRIPTION OF DRAWINGS

FIG. 1 is an exploded perspective view of this invention;

FIG. 2 is a cross-sectional view partly in elevation, of the invention shown in FIG. 1;

FIG. 3 is an elevational view of bezel used with the trephine of this invention and taken along lines 3—3 in FIG. 2;

BEST MODE FOR CARRYING OUT THE INVENTION

Figure 4:
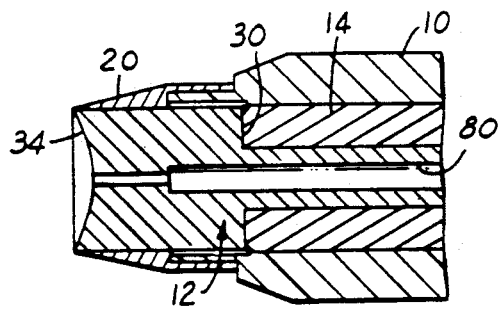
FIG. 4 is a fragmentary view similar to FIG. 2 showing the trephine in its calibration mode, having the blade and cornea stop at the same level.

In the embodiment illustrated in FIGS. 1–10, the instrument 8 includes an outer member or body 10, a cornea stop 12, an inner member or body 14, a handle 16, a centering pin 18, a disposable blade 20 and a bezel 22.

The cornea stop 12 consists of two integral sections, the first is a concentric cylinder forming a plunger or drum 24, having a diameter to allow slidable axial movement within an internal portion 26 of the outer member 10. The second section of the cornea stop 12 is a hollow or tubular shaft 28 which, relative to drum 24, is smaller in diameter. The shaft 28 is joined axially to the center of drum 24.

The point at which the end of shaft 28, and drum 24 meet, forms a shoulder or seat 30 upon which inner body 14 can abut. The end of the shaft 28 opposite seat 30 has threads 32 onto which handle 16 is secured. On the opposite side of the drum 24 from the seat 30 is a cornea engaging surface 34 which is generally semi-circular in shape and engages the cornea during surgery.

The inner body 14 is a concentric cylinder. Threads 36 are located on the external surface 38 of the inner body 14, at the end opposite abutment end 31. Threads 36 cover approximately one third of the external surface 38 of inner body 14. The threads 36 mate with corresponding threads 44 on the inside of the outer body 10.

Affixed to one end of inner body 14, is a pointer 40 and a lever arm 42. Pointer 40 and lever arm 42 both extend radially in opposite directions from one another. Pointer 40 is used to indicate the increment located on bezel 22 which corresponds to the predetermined depth of the incision. Lever arm 42 is used to rotate inner body 14 inside outer body 10, by means of mating threads 36,44 located inside the outer body 10 and on the outer surface of inner body 14. Due to the precision needed for ophthalmic surgery, the threads 36,44 are very precise and fine machined. Threads with a pitch of 0.4 mm are preferred.

The handle 16 has a cylindrical shape, with a textured external surface 46 to assist in gripping during surgery. Handle 16 also has a threaded internal opening 48, which mates with threads 32 on shaft 28 of cornea stop 12.

Outer body 10 has an annular flange 52 with a sloping surface which forms a shoulder 54. A smaller concentric cylinder 56 formed from shoulder 54 forms an annular flange and is adapted for holding the blade 20 thereon. One or more cutouts or openings 60 are formed in the cylinder 56 to allow it to be compressed for installation of a blade 20 thereon and to hold the blade in a tight force-fit relationship.

Bezel 22 is positioned on the external surface 62 of outer body 10, such that it is frictionally rotatable with respect thereto. Bezel 22 has a flange 64 located in a groove 66 which retains bezel 22 on outer body 10, allowing bezel 22 to be frictionally rotated manually relative to the outer body 10. As shown in FIG. 3, the bezel 22 has a series of markings or calibrated increments 68, which correspond to the variable predetermined depths for the blade incision in the cornea (preferably in microns).

On the bezel 22 shown in the drawings (FIG. 3), the scale ranges from 0–400 microns. Where 0.4 mm threads are provided, one revolution of the inner body 14 moves it approximately 400 microns. Whatever scale is utilized, it should be calibrated to the pitch of the threads.

A threaded locking screw 70 mates with a threaded opening 72 in the outer body 10 to lock the outer body 10 and inner body 14 together. The threaded opening 72 is situated on the body 10 adjacent the bezel 22. The outer body 10 and inner body 14 are adapted to be locked together and operated as a single unit once the predetermined depth of the incision has been obtained and the inner body 14 is set in its desired position.

Once outer body 10 and inner body 14 are locked together, they, together with the blade 20, can be moved as one unit. Once the device is centered on the cornea by the centering pin 18 (as explained below), it can be moved forward onto the cornea and the cornea stop positioned thereon. The depth of the incision is precise because outer body 10, inner body 14, and blade 20 all travel forward together as a unit past cornea stop 12, until inner body 14 contacts seat 30 on cornea stop 12 preventing blade 20 from making an incision deeper than the predetermined depth.

The centering pin 18 is an elongated cylindrical rod 74 having a smaller diameter tip portion 76 at one end separated by a shoulder 78. The pin 18 is used to engage a mark previously made on the center of the cornea by conventional techniques. The centering pin 18 is sized to slide freely axially through a channel 80 in the cornea stop 12 so it can engage the cornea at the mark to center the trephine on the eye, and then be withdrawn if desired after the trephine is positioned on the eye.

The basic operation of the unique trephine instrument is depicted in FIGS. 4–10. The surgeon first adjusts the inner body 14 relative to the outer body 10 with lever arm 42 so the outer end of the cornea stop 12 is even with the blade 20 (FIG. 4). In this position, the shoulder or stop 30 is abutted against the front end of the inner body 14. Bezel 22 is then rotated so that the pointer 40 is set to zero. The frictional fit of the bezel on the outer body holds the bezel firmly set in that position.

Figure 5:
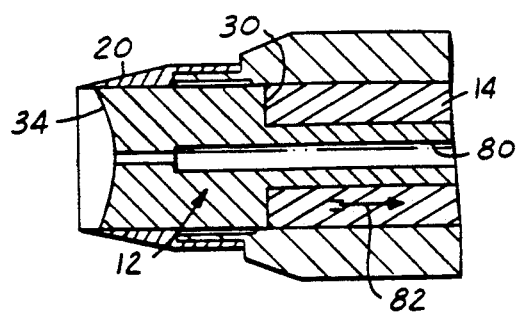
FIG. 5 is fragmentary view similar to FIG. 2 showing the trephine of this invention in its surgical mode with its cutting member at the predetermined operating incision depth.

The lever arm 42 then is used to rotate the inner body 14 and move it axially relative to outer body 10 in the direction of arrow 82 to set the blade 20 at the desired depth of incision relative to cornea stop 12 (FIG. 5). The inner body 14 and outer body 10 are locked together by tightening the screw 70 in the opening 72. The force of the end of the screw bearing on the inner body (either on the threads 36 or the surface 38) holds the two parts firmly together. The screw can be tightened either manually or with a driver or other conventional tool.

Figure 6:
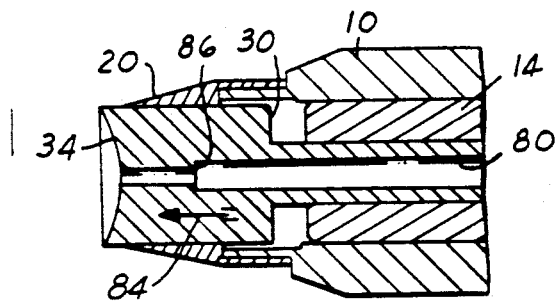
FIG. 6 is a fragmentary view similar to FIG. 2 showing the trephine of this invention with the cornea stop being pushed past the blade in preparation for centering on the eye.

Handle 16 is then slid forward extending cornea stop 12 past the end of the blade 20 in the direction of arrow 84 (FIG. 6). The position of the cornea stop with its cornea engaging surface 34 extending beyond the blade 20 is held in place by manual pressure on or gripping of the handle. For this purpose, the distance D (FIG. 2) between the handle and the inner body can be provided such that when the handle 16 is seated or at rest on the inner body, the cornea stop protrudes an appropriate amount. It is also possible to dimension the drum 24 relative to the blade 20 such that a slight frictional fit exists. In this manner, the cornea stop will stay at a determined position relative to the blade until a manual force is used to move or rotate the blade in order to make the incision.

Figure 7:
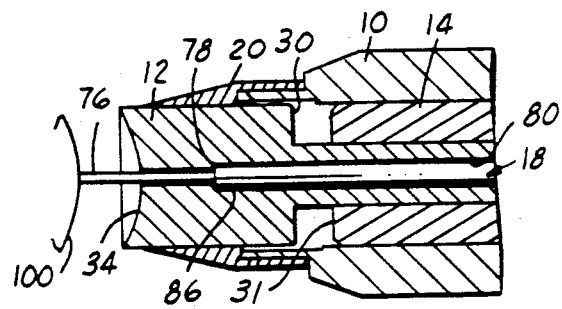
FIG. 7 is a fragmentary view similar to FIG. 2 showing the trephine of this invention being centered on the eye before incision.
Figure 8:
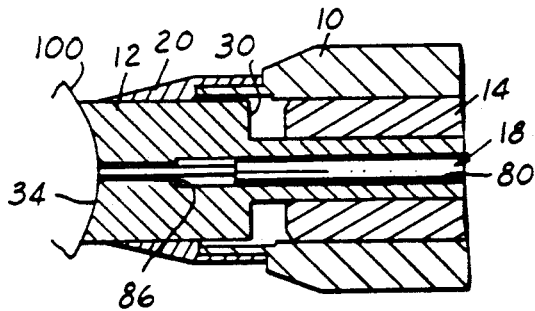
FIG. 8 is a fragmentary view similar to FIG. 2 showing the trephine of this invention in its surgical mode after centering, but before incision.

Centering pin 18 is positioned in channel 80 in the cornea stop. The end of the tip 76 is placed on the cornea 100 at the previously established mark to center the device on the eye (FIG. 7). The shoulder 78 abuts against seat 86 in this position. Once the pin 18 is centered on the eye, the instrument 8 is lowered until the surface 34 is placed on the cornea (FIG. 8). Since the pin is loosely positioned in the channel 80, it will be moved up into the channel as the cornea stop is seated on the eye. The centering pin 18 can be removed entirely from the instrument or left in place, as desired by the surgeon.

The unit formed by the interlocked inner body, outer body and cutting blade is then rotated manually by the surgeon around the handle and cornea stop. The handle can be held in one hand and the unit rotated with the outer. The cornea stop rests firmly on the cornea 100 and does not rotate with the unit. This prevents any undesired pulling, twisting or wrinkling of the cornea surface and any resulting damage to the eye.

Figure 9:
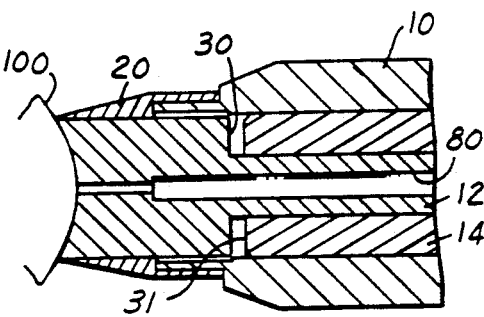
FIG. 9 is a fragmentary view similar to FIG. 2 showing the trephine of this invention as the blade moves toward the cornea just prior to incision.
Figure 10:
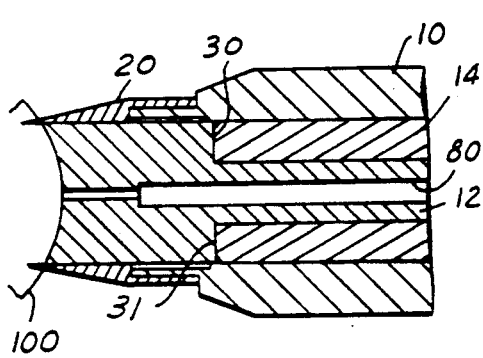
FIG. 10 is a fragmentary view similar to FIG. 2 showing the trephine of this invention, as the incision is made.

As the unit is rotated, a slight downward pressure towards the eye will slide the blade over the drum of the cornea stop until it meets the cornea surface (FIG. 9). Additional downward pressure will cause the tip of the blade to cut into the cornea forming the desired incision (FIG. 10). Penetration of the blade into the cornea 100 is stopped when the end 31 of the inner body meets the shoulder or stop 30 on the cornea stop. At this point, the cornea is cut the desired depth and the instrument is removed from the eye.

The stop 30 prevents the blade from progressing any further into the eye and permits precise cutting to a prespecified depth. After the instrument is removed, the eye is further treated by the surgeon as desired and by conventional means to finish the corrective operation.

As an alternative embodiment, the centering pin 18 can be mounted in the channel 80 with a spring or spring mechanism. The spring can be positioned in the handle 16 or affixed around the tip 76 to the shoulder 78 of centering pin 18. The centering pin 18 in its neutral position will be retracted away from the eye into the internal body of the instrument. To center the trephine, the surgeon applies slight pressure to the centering pin 18 compressing the spring or spring mechanism. Once the instrument is centered, the surgeon, as desired, may release pressure from the centering pin 18 causing it to return to its neutral position. The remainder of the incision procedure is the same as described above. The pin 18 may or may not be removable from the instrument depending on the spring mechanism utilized.

Figure 11:
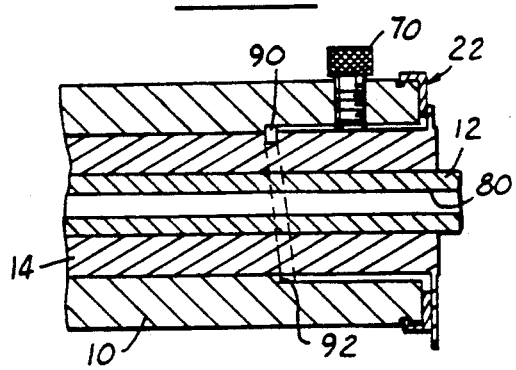
FIG. 11 is a fragmentary view similar to FIG. 2 showing an alternative embodiment of the trephine with a ramp and a shoulder as cooperable means allowing the inner member to rotate and move axially relative the outer member.

Another alternative embodiment utilizes a camming mechanism to translate the inner body relative to the outer body. One such embodiment is shown in FIG. 11. A post 90 is located on the external surface of inner body 14 and cooperates with an inclined ramp 92 located on the inner surface of outer member 10. In operation, the surgeon rotates lever arm 42 to move the post 90 along the ramp 92 to set the blade to the desired depth of incision relative to cornea stop by having inner body 14 and outer body 10 move in opposite directions to each other. The locking screw 70 holds the two bodies together in the same manner as stated above, and the remainder of the operation is completed also in the same manner as specified above.

Alternatively, the post 90 can be positioned on the inner surface of the outer body, or positioned through the outer body. Also, a spiral channel in the inner or outer body (as desired) can be utilized in place of the ramp or shoulder 92.

Although particular embodiments of the present invention have been illustrated in the accompanying drawings and described in the foregoing detailed description, it is to be understood that the present invention is not to be limited to just the embodiments disclosed, but that they are capable of numerous rearrangements, modifications and substitutions without departing from the scope of the claims hereafter.

What is claimed is:

1. An ophthalmic device for making incisions of predetermined depth in the cornea of the eye, said device comprising:
   an outer body;
   an inner body;
   adjustment means for axially adjusting said inner body relative to said outer body corresponding to the predetermined incision depth;
   blade means affixed to said outer body at one end;
   cornea engaging means positioned in said inner body and being axially slidable relative thereto;
   securing means for locking said outer body and inner body together; and
   limit means for preventing incision of the cornea beyond the predetermined depth.

2. The ophthalmic depth in accordance with claim 1 wherein said limit means comprises stop means on said cornea engagement means and mating abutment means on said inner body.

3. The ophthalmic device in accordance with claim 1 further comprising centering pin means positioned in said cornea engaging means and being axially slidable relative thereto, said centering pin being used to centrally position said ophthalmic device relative to the cornea.

4. The ophthalmic device in accordance with claim 1 wherein said blade means is removably affixed to said outer body whereby said blade means can be replaced for subsequent use of the ophthalmic device.

5. The ophthalmic device in accordance with claim 1 further comprising means for measuring the axial adjustment of said inner body relative to said outer body in order to set the incision depth to the predetermined amount.

6. The ophthalmic device in accordance with claim 1 wherein said adjustment means includes mating thread means on said inner and outer bodies and rotation indication and facilitation means.

7. An ophthalmic device for making incisions of predetermined depth in the cornea of the eye, said device comprising:
   an outer body;
   an inner body having an abutment means, said inner body rotatable relative to said outer body and including means cooperable between said bodies to cause said outer body and said inner body to move relatively axially to each other for a predetermined distance when said inner body is rotated relative to said outer body to locate said abutment means;
   a cornea engaging means axially slidably moveable with respect to said inner body and having at one end a handle for moving said cornea engaging means in one direction against said abutment means and in another direction for engaging a cornea;
   blade means affixed to said outer body for movement therewith and;
   locking means for locking said outer body with respect to said inner body after said abutment means is located whereby to position said blade means with respect to said cornea positioning portion for making an incision when said positioning portion is against said abutment means.

8. The device of claim 7 wherein said inner body and said outer body are concentric cylinders.

9. The device of claim 7 including a centering pin axially slidably moveable with respect to said cornea engaging means and adapted to slidably move in one direction to engage the cornea to locate the center of the eye so as to centrally position said outer body with respect to the cornea.

10. The device of claim 7 including a pointer rotatable with said inner body and a bezel rotatably frictionally connected to said outer body adjacent said pointer and calibrated to gauge said predetermined distance whereby to enable incisions of predetermined depth.

11. The device of claim 10 including an arm attached to said inner body opposite to said pointer and useable to adjust the rotation of said inner body relative to said outer body to set said predetermined distance.

12. The device of claim 7 wherein said blade means are removable from said outer body for replacement.

13. The device of claim 7 wherein said cooperable means includes threads on the internal surface of said outer body and matching threads on the outer surface of said inner body.

14. The device of claim 13 including a pointer rotatable with said inner body and a bezel frictionally connected to one end of said outer body adjacent said pointer and calibrated to gauge said predetermined distance whereby to enable incisions of predetermined depth and wherein the axial movement of the inner body relative to the outer body corresponds to said predetermined distance.

15. The device of claim 7 wherein said cooperable means includes a boss on one of said outer body or said inner body and a ramp on the other of said bodies.

16. The device of claim 15 including a pointer rotatable with said inner body and a bezel rotatably frictionally connected to one end of said outer body adjacent said pointer and calibrated to gauge said predetermined distance whereby to enable incisions of predetermined depth and wherein the slope of said ramp cooperates with said boss in accordance with the calibration on said bezel to provide a read-out of said predetermined distance.

17. The method of positioning a concentrically segmented trephine on the cornea of an eye and making an incision of predetermined depth in the cornea with a blade on a segment of the trephine and comprising the steps of:
   axially moving a first concentric segment of the trephine relative to a second concentric segment thereof to position said blade for an incision of predetermined depth,
   locking said first and second concentric segments together,
   axially moving a third concentric segment relative to said locked together first and second concentric segments to position said trephine relative to the cornea in advance of said blade, axially moving a fourth concentric segment relative to said third concentric segment to locate a mark on the center of the eye to center the trephine,
   advancing said locked together segments and said blade toward said cornea while said third concentric segment maintains the position of said trephine on said cornea, and
   rotating said locked together segments to predetermined depth.

* * * * *

UNITED STATES PATENT AND TRADEMARK OFFICE
CERTIFICATE OF CORRECTION

PATENT NO.　　:　　5,084,059
DATED　　　　:　　January 28, 1992
INVENTOR(S)　:　　Daniel J. Metzger It is certified that error appears in the above-identified patent and that said Letters Patent is hereby corrected as shown below:

Column 2, line 37;　　after "edge" delete --of-- and insert --on--.

Column 8; lines 64-65;　　after "to" insert --cause said blade to make said incision to said--.

Signed and Sealed this

Twenty-fifth Day of May, 1993

Attest:

MICHAEL K. KIRK

Attesting Officer　　Acting Commissioner of Patents and Trademarks